(12) United States Patent
Lara et al.

(10) Patent No.: US 10,265,517 B2
(45) Date of Patent: Apr. 23, 2019

(54) RECONFIGURABLE BIOSIGNAL PROCESSING ARCHITECTURE

(71) Applicant: HI LLC, Los Angeles, CA (US)

(72) Inventors: Antonio H. Lara, Los Angeles, CA (US); Roman Sandler, Los Angeles, CA (US); Brian S. Robinson, Los Angeles, CA (US); Kristopher Anderson, Santa Monica, CA (US); Christian Wentz, Providence, RI (US); Randal Koene, San Francisco, CA (US); John W. Stanton, New York, NY (US); Erik J. Peterson, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 10 days.

(21) Appl. No.: 16/022,541

(22) Filed: Jun. 28, 2018

(65) Prior Publication Data

US 2019/0001121 A1    Jan. 3, 2019

Related U.S. Application Data

(60) Provisional application No. 62/527,890, filed on Jun. 30, 2017.

(51) Int. Cl.
*A61N 1/00* (2006.01)
*A61N 1/05* (2006.01)
(Continued)

(52) U.S. Cl.
CPC .......... *A61N 1/0534* (2013.01); *A61B 5/048* (2013.01); *A61B 5/7225* (2013.01);
(Continued)

(58) Field of Classification Search
CPC .............. A61N 1/0534; A61N 1/0531; A61N 1/36064; A61N 1/37252; A61N 1/3787;
(Continued)

(56) References Cited

U.S. PATENT DOCUMENTS 7,209,787 B2  4/2007  DiLorenzo
7,231,254 B2  6/2007  DiLorenzo
(Continued)

FOREIGN PATENT DOCUMENTS

AU   2010295275 B2   10/2013
AU   2014200220 A1    1/2014
(Continued)

OTHER PUBLICATIONS

Cong, Peng, et al. "A 32-channel modular bi-directional neural interface system with embedded DSP for closed-loop operation." European Solid State Circuits Conference (ESSCIRC), ESSCIRC 2014—40th. IEEE, 2014. (4 pages).

(Continued)

*Primary Examiner* — Lindsey G Wehrheim
(74) *Attorney, Agent, or Firm* — ALG Intellectual Property, LLC

(57) ABSTRACT

Devices, systems, and methods herein relate to processing biosignal data. These systems and methods may obtain sensor data from a plurality of electrodes and may also be used to augment cortical function, treat neurological disease, and provide insight and analysis of biological processes and/or clinical therapeutic outcomes. An implantable biosignal processing system may comprise a lead having at least one biosignal sensor configured to transmit biosignal data based on electrophysiological activity of a subject. A first processing system may be coupled to the biosignal sensor and comprise a plurality of analog signal processing circuits configured to be selectively powered based on a (Continued)

selectable treatment mode. A second processing system in communication with the first processing system and may comprise a plurality of digital signal processing circuits configured to be selectively powered based on the treatment mode. A neurostimulator may stimulate tissue according to the set of biosignal characteristics.

30 Claims, 6 Drawing Sheets

(51) Int. Cl.
    *A61N 1/372*     (2006.01)
    *A61N 1/36*     (2006.01)
    *A61B 5/048*     (2006.01)
    *A61N 1/378*     (2006.01)
    *A61B 5/00*     (2006.01)

(52) U.S. Cl.
    CPC ....... *A61N 1/0531* (2013.01); *A61N 1/36064* (2013.01); *A61N 1/3787* (2013.01); *A61N 1/37252* (2013.01); *A61N 1/36067* (2013.01); *A61N 1/36082* (2013.01)

(58) Field of Classification Search
    CPC ............ A61N 1/36067; A61N 1/36082; A61B 5/048; A61B 5/7225
    See application file for complete search history.

(56) References Cited

U.S. PATENT DOCUMENTS

| | | |
|---|---|---|
| 7,242,984 B2 | 7/2007 | DiLorenzo |
| 7,277,758 B2 | 10/2007 | DiLorenzo |
| 7,623,928 B2 | 11/2009 | DiLorenzo |
| 7,853,329 B2 | 12/2010 | DiLorenzo |
| 7,930,035 B2 | 4/2011 | DiLorenzo |
| 7,974,696 B1 | 7/2011 | DiLorenzo |
| 8,380,325 B2 | 2/2013 | McDonald |
| 8,396,557 B2 | 3/2013 | DiLorenzo |
| 8,571,665 B2 | 10/2013 | Moffitt et al. |
| 8,583,237 B2 | 11/2013 | Bedenbaugh |
| 8,712,542 B2 | 4/2014 | McMorrow et al. |
| 8,818,527 B2 | 8/2014 | Ayanoor-Vitikkate et al. |
| 8,934,979 B2 | 1/2015 | Moffitt |
| 8,936,630 B2 | 1/2015 | Denison et al. |
| 9,008,782 B2 | 4/2015 | Kast et al. |
| 9,031,658 B2 | 5/2015 | Chiao et al. |
| 9,042,988 B2 | 5/2015 | DiLorenzo |
| 9,113,801 B2 | 8/2015 | DiLorenzo |
| 9,320,900 B2 | 4/2016 | DiLorenzo |
| 9,333,361 B2 | 5/2016 | Li et al. |
| 9,421,373 B2 | 8/2016 | DiLorenzo |
| 9,427,572 B2 | 8/2016 | Kast et al. |
| 9,561,362 B2 | 2/2017 | Malinowski |
| 9,616,220 B2 | 4/2017 | Romero et al. |
| 9,937,344 B2 | 4/2018 | Starkebaum et al. |
| 9,956,419 B2 | 5/2018 | Bokil |
| 2005/0021103 A1 | 1/2005 | DiLorenzo |
| 2005/0021104 A1 | 1/2005 | DiLorenzo |
| 2005/0119703 A1 | 6/2005 | DiLorenzo |
| 2005/0240242 A1 | 10/2005 | DiLorenzo |
| 2007/0073355 A1 | 3/2007 | DiLorenzo |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0208212 A1 | 9/2007 | DiLorenzo |
| 2008/0119900 A1 | 5/2008 | DiLorenzo |
| 2009/0112282 A1 | 4/2009 | Kast et al. |
| 2009/0157141 A1 | 6/2009 | Chiao et al. |
| 2010/0023089 A1 | 1/2010 | DiLorenzo |
| 2011/0125077 A1 | 5/2011 | Denison et al. |
| 2011/0125078 A1 | 5/2011 | Denison et al. |
| 2012/0203131 A1 | 8/2012 | DiLorenzo |
| 2012/0259389 A1 | 10/2012 | Starkebaum et al. |
| 2013/0324892 A1 | 12/2013 | Zhu et al. |
| 2014/0288620 A1 | 9/2014 | DiLorenzo |
| 2015/0209578 A1 | 7/2015 | Kast et al. |
| 2015/0223710 A1 | 8/2015 | Cong et al. |
| 2015/0375006 A1 | 12/2015 | Denison et al. |
| 2016/0235352 A1 | 8/2016 | DiLorenzo |
| 2016/0296759 A1 | 10/2016 | Cong et al. |
| 2016/0303376 A1 | 10/2016 | Dinsmoor et al. |
| 2017/0151438 A1 | 6/2017 | Orinski |
| 2017/0157404 A1 | 6/2017 | Moffitt et al. |
| 2017/0157410 A1 | 6/2017 | Moffitt et al. |
| 2017/0281927 A1 | 10/2017 | Orinski |
| 2017/0281928 A1 | 10/2017 | Orinski |
| 2018/0071512 A1 | 3/2018 | Feldman et al. |
| 2018/0085593 A1 | 3/2018 | Fayram et al. |

FOREIGN PATENT DOCUMENTS

| | | |
|---|---|---|
| AU | 2016342197 A1 | 6/2018 |
| CA | 3002841 A1 | 4/2018 |
| CN | 102725021 A | 10/2012 |
| EP | 2480283 A1 | 8/2012 |
| EP | 2504060 A2 | 10/2012 |
| WO | WO2005051306 A2 | 6/2005 |
| WO | WO2005051306 A3 | 6/2005 |
| WO | WO2005067599 A2 | 7/2005 |
| WO | WO2005067599 A3 | 7/2005 |
| WO | WO2006017277 A2 | 2/2006 |
| WO | WO2006017277 A3 | 2/2006 |
| WO | WO2009051965 A1 | 4/2009 |
| WO | WO2011035311 A1 | 3/2011 |
| WO | WO2011066320 A2 | 6/2011 |
| WO | WO2011066320 A3 | 6/2011 |
| WO | WO2017070372 A1 | 4/2017 |
| WO | WO2018071906 A1 | 4/2018 |

OTHER PUBLICATIONS

Liu, Xilin, et al. "A 12-channel bidirectional neural interface chip with integrated channel-level feature extraction and PID controller for closed-loop operation." Biomedical Circuits and Systems Conference (BioCAS), 2015 IEEE. IEEE, 2015. (4 pages).

Peterson, Erik J., et al. "Stimulation artifact rejection in closed-loop, distributed neural interfaces." European Solid-State Circuits Conference, ESSCIRC Conference 2016: 42nd. IEEE, 2016. (4 pages).

A. T. Avestruz, et al., "A 5µW/Channel Spectral Analysis IC for Chronic Bidirectional Brain-Machine Interfaces," Solid-State Circuits, IEEE Journal of, vol. 43, pp. 3006-3024, 2008. (19 pages).

Srinivasa R. Sridhara, et al., "Microwatt Embedded Processor Platform for Medical System-on-Chip Applications." Solid-State Circuits, IEEE Journal of, vol. 46, pp. 721-730, 2011. (10 pages).

K. Paralikar, et al., "An implantable 5mW/channel dual-wavelength optogenetic stimulator for therapeutic neuromodulation," Journal of IEEE Solid-State Circuits, vol. 46, issue 1, pp. 321-332, 2011. (3 pages).

Scott Stanslaski, et al., "Design and Validation of a Fully Implantable, Chronic, Closed-Loop Neuromodulation Device With Concurrent Sensing and Stimulation," IEEE Transactions on Neural Systems and Rehabilitation Engineering, vol. 20, Issue 4, pp. 410-421, 2012. (12 pages).

Priori, Alberto, et al. "Adaptive deep brain stimulation (aDBS) controlled by local field potential oscillations." Experimental neurology 245 (2013): 77-86. (10 pages).

Yin, Ming, et al. "A 100-channel hermetically sealed implantable device for chronic wireless neurosensing applications." IEEE transactions on biomedical circuits and systems 7.2 (2013): 115-128. (14 pages).

Beuter, Anne, Jean-Pascal Lefaucheur, and Julien Modolo. "Closed-loop cortical neuromodulation in Parkinson's disease: An alternative to deep brain stimulation?." Clinical Neurophysiology 125.5 (2014): 874-885. (12 pages).

Williams, Jordan J., et al. "Differentiating closed-loop cortical intention from rest: building an asynchronous electrocorticographic BCI." Journal of neural engineering 10.4 (2013): 046001. (16 pages).

(56) References Cited

OTHER PUBLICATIONS

Afshar, Pedram, et al. "Validation of chronic implantable neural sensing technology using electrocorticographic (ECoG) based brain machine interfaces." Neural Engineering (NER), 2011 5th International IEEE/EMBS Conference on. IEEE, 2011. (4 pages).

Arlotti, Mattia, et al. "The adaptive deep brain stimulation challenge." Parkinsonism & related disorders 28 (2016): 12-17. (23 pages).

RECONFIGURABLE BIOSIGNAL PROCESSING ARCHITECTURE

CROSS-REFERENCE TO RELATED APPLICATIONS

This application claims priority to U.S. Provisional Patent Application No. 62/527,890, filed Jun. 30, 2017, the disclosure of which is hereby incorporated by reference in its entirety.

TECHNICAL FIELD

Devices, systems, and methods herein relate to neural interfaces that may be used in diagnostic and/or therapeutic applications, including but not limited to a neural implant and/or neural prosthesis.

BACKGROUND

Implantable electrophysiology devices may be employed to receive and process electrical biosignals, and to produce electrical stimulation signals for the purpose of diagnosing and/or treating neurological disease, and in some cases, to augment brain function. Closed-loop devices use the biological signals as an input for an algorithm for the application of electrical stimulations. For example, implantable electrophysiology devices may be used as brain-machine interfaces for affecting closed-loop control of a prosthetic or robotic arm.

Requirements for implantable electrophysiology devices include low-power consumption for longer battery life and improved signal processing capabilities for handling as much neural activity data as possible. The main issue in achieving both goals is that increasing the signal processing capability usually generates increased power consumption.

Therefore, systems, devices, and methods for low-power processing of biosignals in an implantable system may be desirable.

SUMMARY

Disclosed herein are systems and methods for brain stimulation based on neural recordings. The systems may be configured for recording and/or stimulating one or more deep-brain and/or cortical and/or sub-cortical areas. An implantable biosignal processing system may comprise a first processing system in communication with one or more biosignal sensors and a second processing system in communication with the first processing system. In some variations, there may be multiple instances of the first processing system which are each in communication with the second processing system. A first processing system may comprise an analog signal processor that may comprise one or more analog signal processing circuits such that electrical biosignal data (e.g., electrophysiological data) acquired by the biosignal sensors pertaining to a region of the brain may be processed by the one or more analog signal processing circuits to extract features or characteristics of that brain region. The extracted features or characteristics of that brain region may be stored in a memory buffer or cache, and/or transmitted to the second processing system. For example, an analog signal processing circuit may extract action potential (i.e., spike) time, amplitude, and/or electrical activity waveform from the acquired electrical biosignal data (e.g., electrophysiological data), store these features in a data structure or object, and/or transmit the data structure or object to a second processing system. A second processing system may comprise a digital signal processor. A digital signal processor may comprise a plurality of digital signal processing circuits that may each be selectively powered or activated based on a treatment and/or operating mode of the digital signal processor. That is, depending on the treatment and/or operation mode, certain of the plurality of digital signal processing circuits may be connected to a power source and/or otherwise activated, while others of the plurality of digital signal processing circuits may not be connected to the power source and/or otherwise deactivated. In some variations, the treatment mode may be selected from a set of treatment modes. Alternatively or additionally, activation and/or deactivation of each of the plurality of digital signal processing circuits may be based on the acquired biosignals and/or extracted features. In some variations, the one or more analog signal processing circuits may be selectively powered or activated (or deactivated) similar to the digital signal processing circuits. Selective activation or powering of certain analog signal processing circuits and/or digital signal processing circuits may allow the implantable biosignal processing system to process and/or analyze the biosignals to address a plurality of neural conditions. That is, a single implantable biosignal processing system may be configured to customize and/or alter the biosignal processing pathway in accordance with a desired or suitable treatment mode and/or operating mode.

One variation of an implantable biosignal processing system may comprise a lead comprising at least one biosignal sensor configured to couple to a subject and transmit biosignal data representing electrophysiological activity of the subject (e.g., electrophysiological activity of a brain or cortical region), a first processing system in communication with the lead, a second processing system in communication with the first processing system, and a neurostimulator in communication with the second processing system. The first processing system may comprise an analog signal processor that has a plurality of analog signal processing circuits configured to be selectively powered to perform different sets of analog processing functions according to a treatment mode selected from a plurality of treatment modes, where each treatment mode corresponds to a different set of signal processing parameters and circuit processing sequences. The second processing system may comprise a digital signal processor and a power management circuit in communication with the digital signal processor. The digital signal processor may comprise a plurality of digital signal processing circuits configured to be selectively powered by the power management circuit in accordance with the selected treatment mode to perform different sets of digital processing functions. Each digital signal processing circuit may have an independent data and clock controller configured to adjust a clock rate of the digital signal processing circuit based on a biosignal data volume and selected treatment mode. The powered analog and digital signal processing circuits may be configured to serially process the biosignal data to generate a set of biosignal characteristics. The neurostimulator may be configured to stimulate a predetermined region of tissue using the set of biosignal characteristics. In some variations, the second processing system may have a clock generator that generates a system clock signal having a system clock rate, and the clock rate of an individual digital signal processing circuit may be different from the system clock rate. An implantable biosignal processing system may further comprise a third processing system in communication with the first processing system, the second processing system, and the neurostimulator. The third processing system may be configured to activate the neurostimulator based on the set of biosignal characteristics. In some variations, the first processing system may be configured to transmit the set of biosignal characteristics to the third processing system. The biosignal characteristics may comprise one or more waveform parameters. The first processing system may be configured to serially sample a plurality of biosignal sensors of the lead. The second processing system may be configured to validate the biosignal data from the first processing system using one or more filters.

In some variations, there may be multiple instances of the first processing system and associated biosignal sensors. For example, the lead may be a first lead and the at least one biosignal sensor may be a first set of biosignal sensors, and the first processing system may be a first instance of the first processing system, and the system may further comprise a second lead comprising a second set of biosignal sensors and a second instance of the first processing system in communication with the second lead. The second processing system may be in communication with the second instance of the first processing system. Each of first and second instances of the first processing system may be configured to process biosignal data acquired from the first and second leads respectively based on different treatment modes, and the second processing system may be configured to receive the processed biosignal data and/or biosignal characteristics from the first and second instances of the first processing system simultaneously. In some variations, the second processing system may be configured to receive, aggregate, and process the biosignal data from the first and second instances of the first processing system.

Also disclosed herein is a method of processing biosignal data. One variation of a method may comprise selecting at least one treatment mode from a plurality of treatment modes, where each treatment mode corresponds to a different set of signal processing parameters and circuit processing sequences (and optionally, biosignal characteristics), powering a set of analog signal processing circuits of a first processing system to perform different analog processing functions based on the treatment mode and powering a set of digital signal processing circuits of a second processing system to perform different digital processing functions and processing sequences according to the selected treatment mode, acquiring biosignal data from a lead comprising at least one biosignal sensor, transmitting the acquired biosignal data to the first processing system, processing the biosignal data using the powered analog signal processing circuits, transmitting the processed biosignal data to the second processing system, adjusting clock rates for each of the powered digital signal processing circuits according to the selected treatment mode, generating a set of biosignal characteristics based on the processed biosignal data using the powered digital signal processing circuits, and transmitting the set of biosignal characteristics to a neurostimulator. The treatment modes may be configured to power different sets of analog signal processing circuits and digital signal processing circuits. The method may optionally comprise generating a neurostimulator control signal based on the set of biosignal characteristics, and activating the neurostimulator according to the neurostimulator control signal. In some variations, signal processing parameters, circuit processing sequences, and data output size of the digital signal processing circuits may be determined based the selected treatment mode.

Another variation of an implantable biosignal processing system may comprise a first processing system comprising an analog signal processor having a plurality of analog signal processing circuits, and a second processing system in communication with the first processing system. The first processing system may be configured to connect to a lead comprising one or more biosignal sensors for acquiring electrophysiological data of a brain region of a subject, and the second processing system may comprise a digital signal processor having a power management circuit and a plurality of digital signal processing circuits in communication with the power management circuit. The power management circuit may be configured to selectively activate and/or deactivate digital signal processing circuits based on a treatment mode of the second processing system to generate a set of electrophysiological data characteristics. Each digital signal processing circuit may have a data and clock controller configured to adjust a clock signal of the digital signal processing circuit based on at least one characteristic of the electrophysiological data. Activating a digital signal processing circuit of the plurality of digital signal processing circuits may comprise powering on the digital signal processing circuit, and deactivating a digital signal processing circuit may comprise powering off the digital signal processing circuit. The first processing system may further comprise a signal processing controller that selectively activates and/or deactivates the plurality of analog signal processing circuits according to the treatment mode. The data and clock controller may be configured to activate the digital signal processing circuit in a parallel processing configuration if a data volume of the electrophysiological data meets or exceeds a predetermined data volume threshold and to activate the digital signal processing circuit in a serial processing configuration if the data volume is bellowed the predetermined data volume threshold. The second processing system may have a first clock signal having a first clock rate and each of the plurality of digital signal processing circuits may have a second clock signal having a second clock rate generated by the data and clock controller. When the digital signal processing circuit is in a parallel processing configuration, the second clock rate may be less than the first clock rate, and when the digital signal processing circuit is in a serial processing configuration, the second clock rate may be the same as the first clock rate. The first processing system may further comprise a signal processing controller that selectively activates and/or deactivates the plurality of analog signal processing circuits based on the treatment mode. In some variations, the set of electrophysiological data characteristics may comprise a characteristic selected from the group consisting of: phase, amplitude, or frequency. For example, the set of electrophysiological data characteristics may comprise a phase or amplitude of electrophysiological data in a beta band (about 12.5 Hz-30 Hz) frequency range, and/or the set of electrophysiological data characteristics may comprise a phase or amplitude of electrophysiological data in a gamma band (about 30 Hz-100 Hz) frequency range, and/or the set of electrophysiological data characteristics may comprise action potential count and/or timing and/or amplitude. The treatment mode may be selected from a group consisting of: neurological disease treatment mode, neurological function augmentation mode, or neural circuitry analysis mode. For example, the treatment mode may be a Parkinson's Disease treatment mode, and/or the treatment mode may be an epileptic seizure prevention mode. Some variations may further comprise a neurostimulator in communication with the second processing system and configured to stimulate the brain region of the subject. The second processing system may be configured to generate a neurostimulator control signal based on the set of electrophysiological characteristics. The lead may be a first lead and the system may further comprise a second lead comprising one or more biosignal sensors, and a third processing system that is in communication with the second processing system. The third processing system may have a second plurality of analog signal processing circuits and may be configured to connect to the second lead for acquiring and processing electrophysiological data of a brain region. In some variations, the second processing system may be configured to aggregate and process electrophysiological data from the first processing system and the third processing system according to the treatment mode. The second processing system may be configured to aggregate and process electrophysiological data from the first processing system and the third processing system simultaneously. In some variations, the treatment mode may be a first treatment mode and the neurostimulator control signal may be a first neurostimulator control signal, and the second processing system may be configured to process electrophysiological data from the first processing system according to the first treatment mode to generate the first neurostimulator control signal, and may be further configured to process electrophysiological data from the third processing system according to a second treatment mode to generate a second neurostimulator control signal.

DETAILED DESCRIPTION

Figure 1:
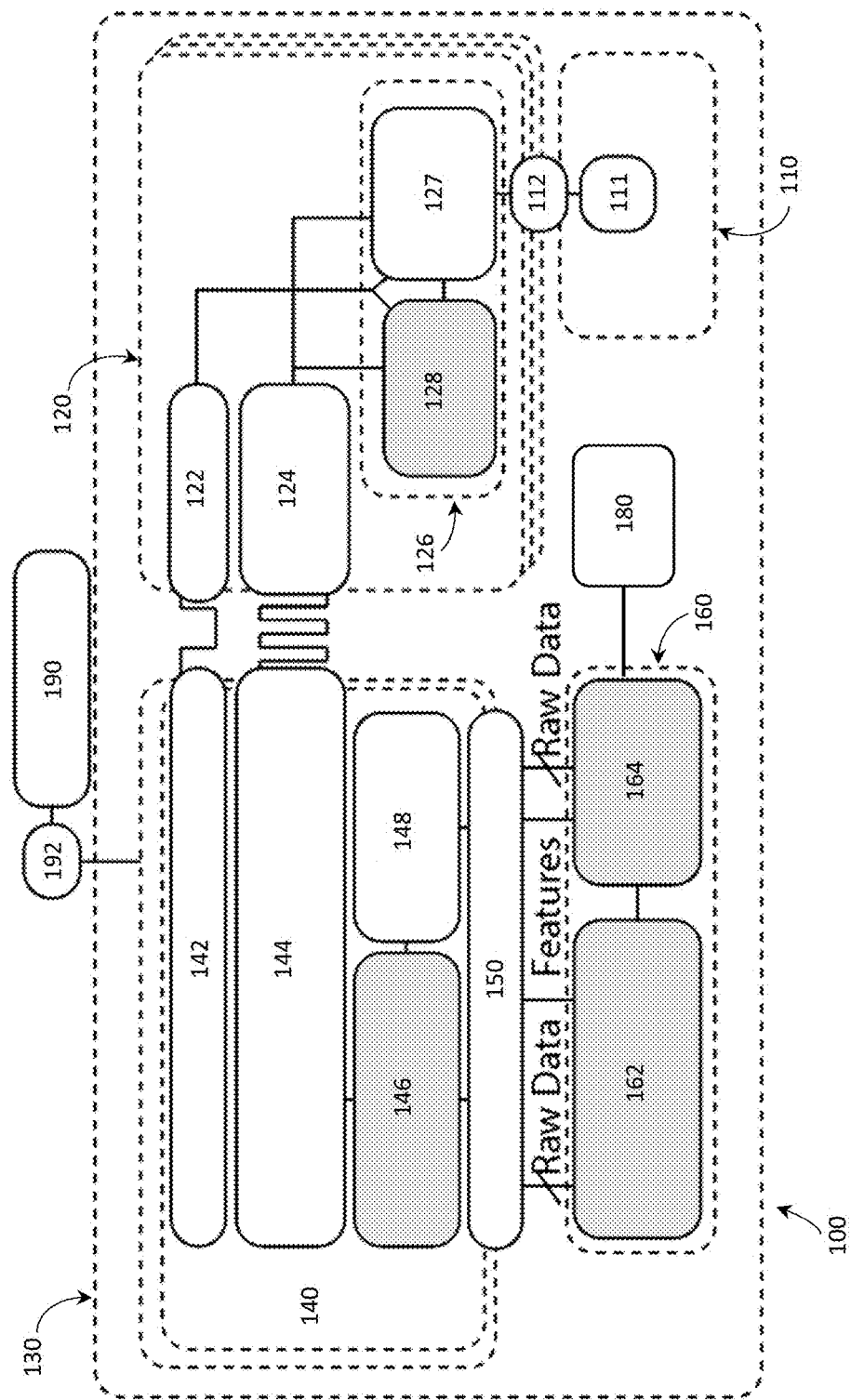
FIG. 1 is a block diagram of an illustrative variation of a biosignal processing system.

Described herein are implantable systems that may measure neural activity and provide electrical stimuli to modulate such activity. Conventional systems may include a set of recording electrodes that may be configured to amplify, digitize, and record neural signals. Some of these systems include a stimulator that may use the processed data to treat neurological disease and/or to augment brain function. However, processing neural signaling data may be difficult in highly scaled fully implanted systems due to power constraints. Furthermore, some stimulators use closed-loop algorithms that may be viable only on a biologically relevant timescale (e.g., millisecond response times similar to biosignaling within tissue) such that data processing offloaded to an external computing device may not be practical due to a lengthy round-trip time of flight. Some conventional solutions rely on custom signal processing circuitry to process biosignals to generate one or more specific data parameters (e.g., data within a narrow frequency band) for input to a stimulator to treat a specific condition (e.g., Parkinson's disease). However, these approaches are neither reconfigurable nor capable of providing multi-function processing (e.g., data processing for diagnosis and treatment of different diseases). Furthermore, these systems typically provide one digital signal processor pathway per electrode channel and therefore does not easily scale as the recording channel count increases.

Described herein are biosignal processing systems and methods for receiving and processing sensor data (e.g., implantable electrode) using a plurality of treatment modes for a fully implanted system without external processing. Each treatment mode may determine a power state (e.g., ON, OFF) of a set of circuit components configured to process biosignal data and generate clinically relevant data for a particular task (e.g., monitoring, diagnosis, disease treatment). For example, different circuit blocks within a signal processor (e.g., analog signal processor, digital signal processor) may be selectively powered and/or clock gated when not in use based on a selected treatment mode, thereby reducing power consumption and increasing the battery life of an implantable processing system. In some variations, the processing system may include a neurostimulator configured to utilize the information extracted from the biosignal to determine stimulation parameters. A neurostimulator may comprise one or more leads, where the leads may include one or more stimulating electrodes and one or more electrode conductor wires corresponding to stimulating electrodes. The electrodes may be connected to the distal end of each conductor wire and may be configured to apply electrical energy (e.g., to inject current or apply a voltage potential) to affect neural activity. Optionally, the leads may also include sensing electrodes or biosignal sensors configured to sense electrophysiological activity of a patient. Alternatively or additionally, a neurostimulator may comprise one or more optical fibers and/or laser and/or LED illumination that affect neural activity by introducing an optical stimulus and/or one or more ultrasound transducers that affect neural activity by introducing an ultrasonic stimulus. For example, a neurostimulator may use the processed biosignal data within a biologically relevant timescale to treat the patient through tissue stimulation. Unlike conventional systems having specific and customized circuit configurations only capable of performing a discrete task, the systems described herein may process biosignal data for a plurality of tasks and in a plurality of ways in a power efficient manner.

An implanted system having a plurality of biosignal sensors may generate a large volume of data for processing (e.g., preprocessing, digitization). Biosignal data processing may be performed within the implanted system, to reduce latency, rather than offloading the biosignal processing to an external device using a power intensive communication link. In particular, processing of large volumes of data may be optimally achieved through localized low-power application-specific implanted architectures. The system architecture (e.g., a fully implanted biosignal processing system) may be reconfigurable and/or scalable to process a variable or predetermined volume of sensor data in order to extract a selectable set of features (e.g., clinically relevant data) from the biosignal data (e.g., electrophysiological activity). For example, the biosignal processing system may be scaled such that higher volumes of data (e.g., from additional electrodes and/or other sensors) may be processed as necessary.

In some variations, the implanted biosignal processing system may extract and store a predetermined set of features (e.g., biosignal characteristics) from the raw data without storing the raw data itself, thereby increasing memory storage efficiency and permitting an increase in recording channel counts and/or longer recording times. For example, rather than storing raw biosignal data in limited memory space, the processing system may generate and store a set of biosignal characteristics such as sensor identifier, spike time(s), amplitude, and waveform from a set of templates. The number of bits required to encode these features may be based on the number of biosignal sensors, waveform templates, and dynamic range of the system.

The hardware of the system is reconfigurable and flexible enough to generate appropriate input for a plurality of closed-loop algorithms (e.g., stimulation therapy). For example, the systems and methods may have various modes of operation (e.g., treatment modes) for various applications, including but not limited to augmenting cortical function, treating neurological disease, and providing insight and analysis of biological processes and/or neural circuitry and function, and/or clinical therapeutic outcomes using the processed sensor data. For example, data output from the biosignal processing system may be useful for closed-loop stimulation, clinical algorithm development, and/or analysis of neural circuits.

In some variations, the biosignal processing system may include a plurality of biosignal sensors configured to sense electrophysiological activity of a patient and may be pre-processed by an analog signal processor in the analog domain from raw, unsampled sensor data. The preprocessed biosignal data may represent a set of desired biosignal characteristics (e.g., features) useful as input to a closed-loop algorithm. The processed analog data may be processed by a digital signal processor to normalize and validate the sensor data (e.g., using one or more filters to remove artifacts and/or junk data). The analog and digital signal processors may be power and clock gated to power OFF circuit blocks not in use for the selected treatment mode. The processed data may be output to a stimulator (e.g., neurostimulator) of the system. The stimulator may comprise a classifier configured to receive the processed data and determine stimulation parameters (e.g., waveform, amplitude, frequency, and phase). For example, the classifier may receive processed biosignal data and determine that tissue stimulation frequency and amplitude should be increased based on the sensor data. A predetermined region of tissue may be stimulated using one or more stimulating electrodes, where the stimulation waveform parameters are delivered using stimulation programs stored in the neurostimulator.

Generally, the systems and methods described herein may receive sensor data from a set of biosignal sensors (e.g., biosignal sensors on a lead) coupled to a first processing system including an analog signal preprocessor and a second processing system including a digital signal processor (DSP). Signal characteristics from electrophysiological signal data such as frequency, amplitude, and phase may be used to understand neurological circuits, provide clinical/therapeutic insight, and/or enable closed-loop algorithms to augment cortical functioning or treat neurological disease. For example, a Parkinson's disease treatment mode of the biosignal processing system may be selected to process the raw sensor signal data to extract beta-band information (e.g., about 12.5-30 Hz) as a set of biosignal characteristics by powering a predetermined set of analog processing circuits. However, a spike processing mode may be selected to detect action potentials and/or high frequency (e.g., about 1-10 kHz) electrophysiological activity. Such mode may be used, for example, to detect an onset of an epileptic event and/or to apply a treatment stimulation to help prevent a full episode and/or reduce neural activity associated with an epileptic seizure. Components of the analog and digital signal processors may be selectively powered for each of these modes to lower power consumption.

The analog signal preprocessor may be configured to extract one or more selectable signal characteristics (e.g., time domain features) from the sensor data, as well as perform filtering, frequency domain conversion, differencing, summation, multiplication, and other signal conditioning functions. The extracted features may be transmitted with the sensor data to the second processing system. The digital signal processor may select and execute a predetermined function on the data from the first processing system for a predetermined time period (e.g., computing cycle). The digital signal processor may be configured to perform one or more functions including outlier correction, digital re-referencing, discrete Fourier transform, fixed-point digital arithmetic, digital filtering, averaging, windowing, and the like. Circuit components corresponding to unused signal processing functions may be turned OFF on a per application basis corresponding to a treatment mode (e.g., monitoring, diagnosis, treatment).

In some variations, the output of the biosignal processing system may be used as input for a third processing system (e.g., a closed-loop stimulator) to provide therapeutic treatment to a subject. For example, a neurostimulator may use the set of biosignal characteristics and/or processed biosignal data to determine waveform parameters for stimulating one or more predetermined regions of tissue. One or more stimulating electrodes of the neurotransmitter may be used to stimulate one or more predetermined regions of tissue.

In some variations, the systems and methods disclosed herein may be scalable such that a predetermined number of biosignal processing systems may be configured to operate in parallel based on the application and other criteria. The signal features extracted may be configured on a per application basis to optimize data processing speed and power consumption.

I. Systems

Overview

Described herein are biosignal processing systems for use in measuring, processing, analyzing, and/or stimulating electrophysiological activity in a subject. FIG. 1 is a block diagram of an illustrative variation of a biosignal processing system (100) that may be configured to be fully implanted in a subject. The biosignal processing system (100) may comprise at least one lead (110) which may include one or more biosignal sensors (111) configured to sense electrophysiological activity of a patient, a first processing system (120) (e.g., analog processing system, satellite ASIC), a second processing system (130) (e.g., digital processing system, Hub ASIC), and a third processing system (160) (e.g., neurostimulator, controller, application processor (AP)). The one or more leads (110) may be coupled to the first processing system (120) via a first feed through (112) (FT) such as an electrical connector. In some variations, one or more second sensors (190) (e.g., digital sensors that measure characteristics such as pH, conductivity, dissolved oxygen, temperature, etc.) may be coupled to the second processing system (130) via a second feed through (192).

In some variations, the second processing system (130) may be coupled to a plurality of first processing systems (120), each coupled to a plurality of leads (110). For example, the second processing system (130) may aggregate and process data received from N first processing systems (120) (e.g., N=4). The one or more leads (110) may comprise one or more biosignal sensors that may be configured to provide data to the first processing system (120) by one or more conductor wires corresponding to the one or more biosignal sensors. In some variations, a biosignal sensor may comprise an electrode that measures electrophysiological activity and/or signals which may be transmitted to a processor (e.g., having an analog-to-digital converter, and/or an amplifier, and/or filter, etc.). A lead may have any number of biosignal sensors, as may be desirable. For example, a lead (110) may comprise from about 10 biosignal sensors to about 20 biosignal sensors, from about 20 biosignal sensors to about 30 biosignal sensors, from about 30 biosignal sensors to about 40 biosignal sensors, from about 90 biosignal sensors to about 100 biosignal sensors, from about 101 biosignal sensors to about 200 biosignal sensors, etc. This configuration of a hub (second processing system) coupled to a plurality of satellites (first processing systems) allows leads to be implanted in different parts of the brain, thereby allowing data from several cortical regions to be aggregated and processed in parallel. For example, data acquired in one region of the brain may be processed and used to control therapeutic stimulation in another region of the brain. Additionally or alternatively, the signal processing pathway of the implanted biosignal processing system may be reconfigurable for a plurality of therapeutic indications. For example, different treatment modes may power different sets of satellite ASICS and sensors, and may also process the biosignals using different circuit components.

The first processing system (120) may include a command interface (122) configured to control the first processing system (120) and a first transceiver (124) such as a low-voltage differential signal (LVDS) transmitter configured to communicate with the second processing system (130) and/or other first processing systems (120) (not shown). The command interface (122) and the first transceiver (124) may be coupled to an analog front end (126) (AFE). The analog front end (126) may include an amplifier (127) and an analog signal processor (128) (e.g., analog preprocessor). The amplifier (127) may be configured to provide gain and/or signal filtering to the sensor signal received from the sensor (110). The amplifier (127) may comprise, for example, a low noise amplifier (LNA). The analog signal processor (128) may be configured to extract time domain features (e.g., amplitude envelope) from the biosignal, and perform additional processing including, but not limited to, analog filtering, time-to-frequency domain conversion, power spectral density, and differencing/multiplication. The analog signal processing may quickly extract features or clinically relevant biosignal data characteristics that may be used to inform treatment. The analog signal processor (128) is described in more detail with respect to FIG. 2. Performing the initial signal processing within the analog domain may significantly save power and reduce latency relative to processing on a microcontroller or external computing device. The first processing system (120) may output a set of raw biosignal data and a set of biosignal characteristics in a data frame having a predetermined time frame to the second processing system (130). The data frame may represent a snapshot in time of the biosignal data from the sensors coupled to the first processing system (120) and include extracted features derived therefrom.

The second processing system (130) may include a control or analysis circuit (140) having a command interface (142) configured to control the second processing system (130) and/or one or more first processing systems (120). The control or analysis circuit (140) may include a second transceiver (144) such as an LVDS receiver, a digital signal processor (146) (e.g., digital preprocessor), and a power management circuit (148). The power management circuit (148) may comprise a set of data and clock controllers for each circuit component of the digital signal processor (146) (e.g., circuit blocks (326-336) in FIG. 3A) and which are configured to independently power and/or clock gate each of the circuit components so as to control a power ON/OFF state of the component. For example, power and/or clock gates may operate by shutting off the current to circuit components that are not in use. The clock controller may be configured to vary a clock rate of each of the circuit components to control an operating frequency of that component. For example, the clock controller of an FFT circuit (336) may increase the FFT's clock rate by a predetermined multiplier relative to that of the digital signal processor as a whole when operating, for example, under a Parkinson's disease treatment mode. This reconfigurability may help facilitate faster processing for larger volumes of data than would otherwise be achieved.

The second transceiver (144) may be configured to receive the data frame from the first transceiver (124) of the first processing system (120). An input/output interface (150) may be configured to couple to a third processing system (160). Data frames may be aggregated by the second processing system (130) and processed after N samples have been received. For example, for a Parkinson's disease mode, N may be one thousand samples such as one second of data sampled at 1 kHz. The digital signal processor (146) may unpack the data frame to separate the raw biosignal data from the set of biosignal characteristics.

As described in more detail with respect to FIG. 3, the digital signal processor (146) may be configured to normalize and validate the data. The digital signal processor (146) may be configured to process data serially, that is, in a series of processing steps executed in a predetermined order. Each processing step, or cycle, is understood herein as the execution of one DSP or mathematical function (e.g., processing in one circuit block) on the dataset. After completion of a processing cycle, the digitally processed data may be stored in memory. The data may then be retrieved from memory and input into a different circuit block of the DSP for the subsequent processing cycle. The processed data may be stored in an output data buffer. The number of samples, as well as the processing steps may be determined on a per application basis.

Alternatively, the second processing system (130) may receive and process the raw biosignal data aggregated from a plurality of first processing systems (120) using the digital signal processor (146) to extract features or clinically relevant biosignal data characteristics that may be used to inform a type of treatment, such as a Parkinson's disease treatment mode.

The third processing system (160) may include one or more controllers configured to control a stimulator (180) using the processed digital data output by the second processing system (130). The controllers may include one or more of an FPGA (162) and microcontroller (164). The stimulator (180) may include one or more leads, each lead comprising one or more stimulating electrodes. Additionally or alternatively, the third processing system (160) may also receive the raw sensor data from the biosignal sensors (e.g., of lead(s) (110)). A power source (e.g., battery) may be coupled to one or more of the first processing system (120), second processing system (130), and third processing system (160). In some variations, the third processing system may comprise a classifier configured to control the stimulator (180).

First Processing System

Figure 2:
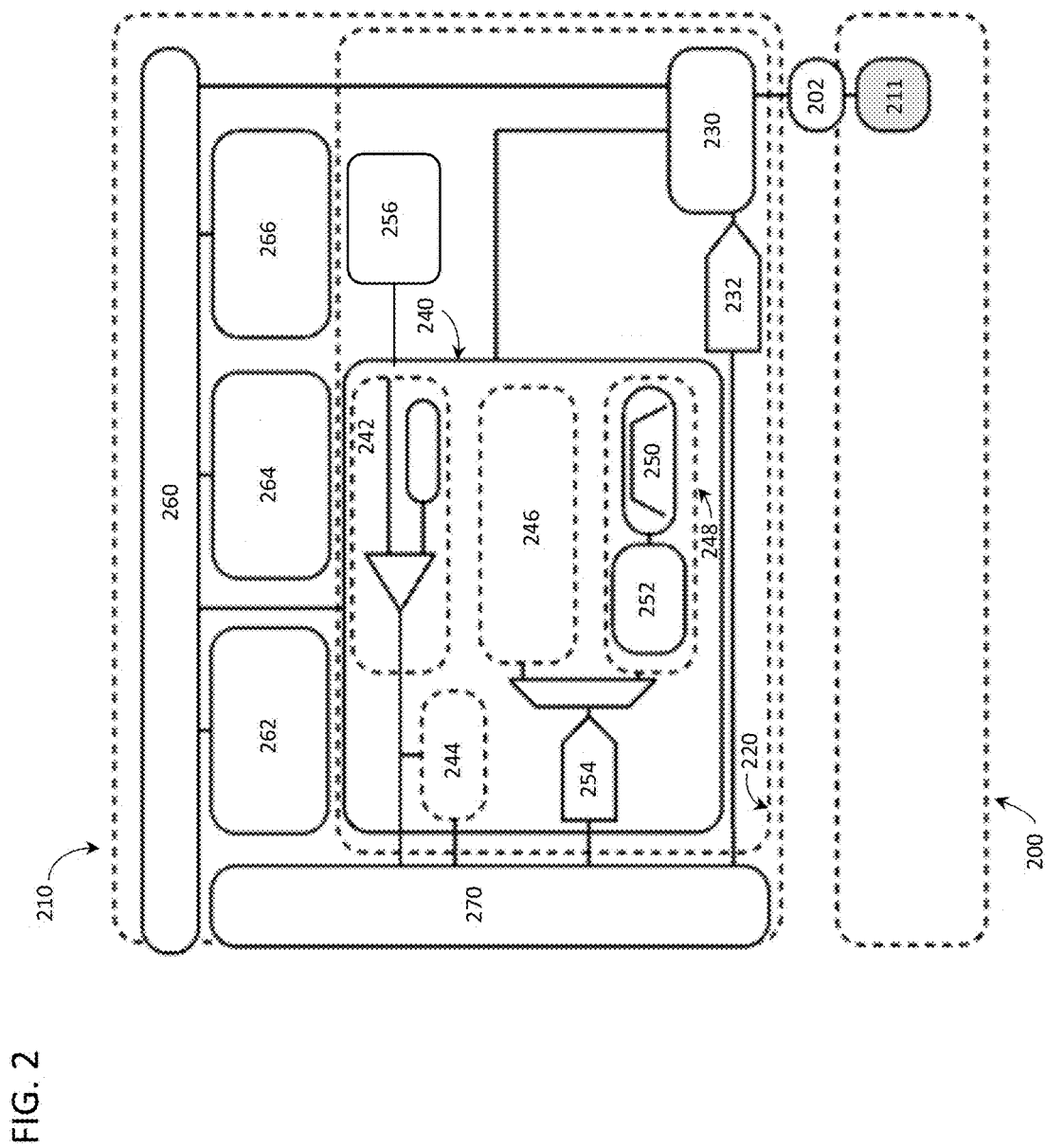
FIG. 2 is a block diagram of an illustrative variation of a first processing system of a biosignal processing system.

FIG. 2 is a block diagram of an illustrative variation of a first processing system (210) of a biosignal processing system. One or more leads (200) comprising plurality of biosignal sensors (211) (e.g., which may be electrodes, as described above) may be coupled to the first processing system (210). The biosignal sensors of lead (200) may be serially sampled over a predetermined sampling rate window (e.g., a sampling rate of 1 kHz sampled over a 1 ms period). The first processing system (210) may include a command interface (260) configured to control the first processing system (210) and a first transceiver (270) such as an LVDS transmitter configured to communicate with other processing systems (not shown). The command interface (260) may be coupled to analog front end (220), internal control circuit (262), artifact suppression circuit (264), and electrode impedance spectroscopy circuit (266). The analog front end (220) may include analog signal processor (240) (e.g., analog preprocessor), amplifier (230), and analog-to-digital converter (232) (ADC). The amplifier (230) may comprise a low noise amplifier. The analog signal processor (240) may comprise a plurality of selectable signal pathways.

FIG. 2 illustrates three analog signal processing circuits (e.g., signal processing pathways) of the analog processor (240). The analog thresholding circuit (242) may comprise a digital-to-analog converter (DAC), a comparator, and a counter (244) and be configured to compare the raw biosignal data against a per-sensor adjustable threshold voltage value set by the DAC. The comparator may compare two signals (e.g., voltages, currents) and output a signal indicating which is larger. The counter (244) may be a sequential circuit used for counting pulses. The counter (244) may be configured to count the number of times the voltage threshold has been exceeded over a sampling period. The analog processor (240) may include a single frequency range (e.g., single bin) power-spectral-density (PSD) circuit (246) and an instantaneous phase and amplitude circuit (248) (P/A). The instantaneous phase and amplitude circuit (248) may operate over an adjustable frequency range (e.g., about 10-30 Hz, about 30-80 Hz), which may be first filtered using a tunable a-pole analog filter and then sampled by the P/A circuit (248).

In some variations, electrophysiological activity received at the biosignal sensors of lead (200) first proceeds through the feed through (202) (FT) to an LNA/Gain/Filtering stage (230), which drives an ADC (232) as well as the analog signal processor (240). In some variations, a unity gain buffer (not shown) may be provided between the amplifier (230) and the analog signal processor (240) to reduce loading of the amplifier (230). Biosignal data may be processed in the analog signal processor (240) through the analog thresholding circuit (242) and either the PSD (246) or the instantaneous PA (248).

For example, in a Parkinson's disease treatment mode, an analog processing circuit (e.g., analog bandpass filter) of the analog signal processor (240) may be set to about 12.5 Hz to about 30 Hz, and the single bin PSD circuit (246) may powered ON. The other analog processing circuits in the analog signal processor may be powered OFF in the Parkinson's disease treatment mode. Processing of the raw biosignal data may generate a set of analog biosignal characteristics that may be transmitted to a second processing system along with the raw biosignal data for further processing. The output of the analog signal processor may be used as stimulation parameters for a neurostimulator.

In a spike processing mode, an analog processing circuit (e.g., spike detection circuit) of the analog signal processor (240) may be powered ON. The DAC of the analog thresholding unit (242) may be set to use a dynamically updated threshold based on a spike detection algorithm. For example, the analog filter may be set to between about 800 Hz and about 2 kHz for PSD extraction.

In some variations, a treatment mode may be selected and transmitted by the second processing system to the first processing system (210). The treatment mode may correspond to a set of analog and digital signal processing circuits that are powered ON and OFF. Nominally, the entire analog preprocessor is powered OFF to save power. Analog signal processing may be enabled through a request from the second processing system (driven by the clinical algorithm requirements corresponding to the treatment mode), which enables a predetermined set of signal pathways (e.g., through the analog signal processor (240). For example, a voltage or current threshold may be a global threshold (i.e., applicable to every electrode in the implantable device), or each of the plurality of first processing systems may have a local voltage or current threshold that is applied to electrodes associated with that first processing system. The treatment mode may determine whether a local or global threshold is applied to biosignal data acquired on the biosignal sensors. Alternatively or additionally, the threshold applied to biosignal data may be determined by local control logic of the first processing system. In one mode, a global threshold may be applied to the biosignal sensors for performing outlier detection. For example, the global threshold may be set to about 90% of the maximum amplified output level. If most of the biosignal sensors detect biosignals that exceed the global threshold (e.g., the number or percentage of electrodes detecting above-threshold biosignals exceed a threshold), the processing system(s) may interpret that data as a systemic perturbation that may not be relevant to the clinical condition of that patient. For example, if about 60% or more of the biosignal sensors detect above-threshold signals, the processing system may determine that the current data frame is dominated by a motion artifact or by some other global biological event, which may not be relevant to the neural data of clinical interest. As such, this data frame can be regarded as an outlier. In another example, spike detection thresholds applied to biosignal sensors may be determined by the particular first processing system with which the biosignal sensors are associated. In some variations, each individual biosignal sensor may have its own stored DAC code representing the voltage value that must be exceeded to indicate a spike has occurred. This individual electrode's stored code may be dynamically updated using a variety of update algorithms (e.g. a running average, non-linear energy operator, etc.) or any other spiking update algorithm.

Furthermore, a data buffer (256) may be adjusted to accommodate the output data of the analog signal processor (240). For example, the data buffer (256) may comprise one or more data bins (e.g., queues, lists, sub-buffers, etc.) that may store different types of data and/or data that is to be transferred to different processing modules or destinations. For example, the data buffer (256) may comprise a two-bin circular queue or ring buffer, where the first bin corresponds to data being transmitted to the hub or second processing system (e.g., transmitted at time t) and the second bin corresponds to data being accumulated (e.g., that is to be transmitted to the hub or second processing system at time t+1). The first bin may store a first set of data frames comprising raw biosignal data and/or output data from the analog signal processor (240) that is to be transmitted to the hub (or second processing system) at time t. The second bin may store a second set of data frames comprising raw biosignal data and/or output data from the analog signal processor (240) that is to be transmitted to the hub (or second processing system) at time t+1. The first and second sets of data frames may comprise a data frame for each biosignal sensor.

Alternatively or additionally, the data buffer (256) may comprise additional data bins, for example, a four-bin circular queue that further segregates the raw biosignal data from the processed analog signal data. The first bin may store a first set of data frames comprising raw biosignal data to be transmitted to the hub (or second processing system) at time t, the second bin may store a second set of data frames comprising output data from the analog signal processor (240) to be transmitted to the hub (or second processing system) at time t, the third bin may store a third set of data frames comprising raw biosignal data to be transmitted to the hub (or second processing system) at time t+1, and the fourth bin may store a fourth set of data frames comprising output data from the analog signal processor (240) to be transmitted to the hub (or second processing system) at time t+1. The data frames may collectively comprise data from all biosignal sensors of the one or more leads (200). In some variations, the second processing system may receive one data frame per biosignal sensor where the data frame includes the raw biosignal data and the analog signal processor output (e.g., extracted analog features). Alternatively or additionally, the first processing system may transmit raw signals from the biosignal sensors (e.g., sensing electrodes) of the one or more leads (200) to the first transceiver (270) (after amplification and digital conversion), and the first transceiver (270) may transmit the raw data signals to the second processing system for aggregation and further analysis.

In some variations, the first processing system may include individual data controllers and clock controllers (not shown) for each circuit component (e.g., block) such that each component may be powered ON and OFF per application (e.g., treatment mode). Examples of data and clock controller circuits are described below.

Second Processing System

Figure 3A:
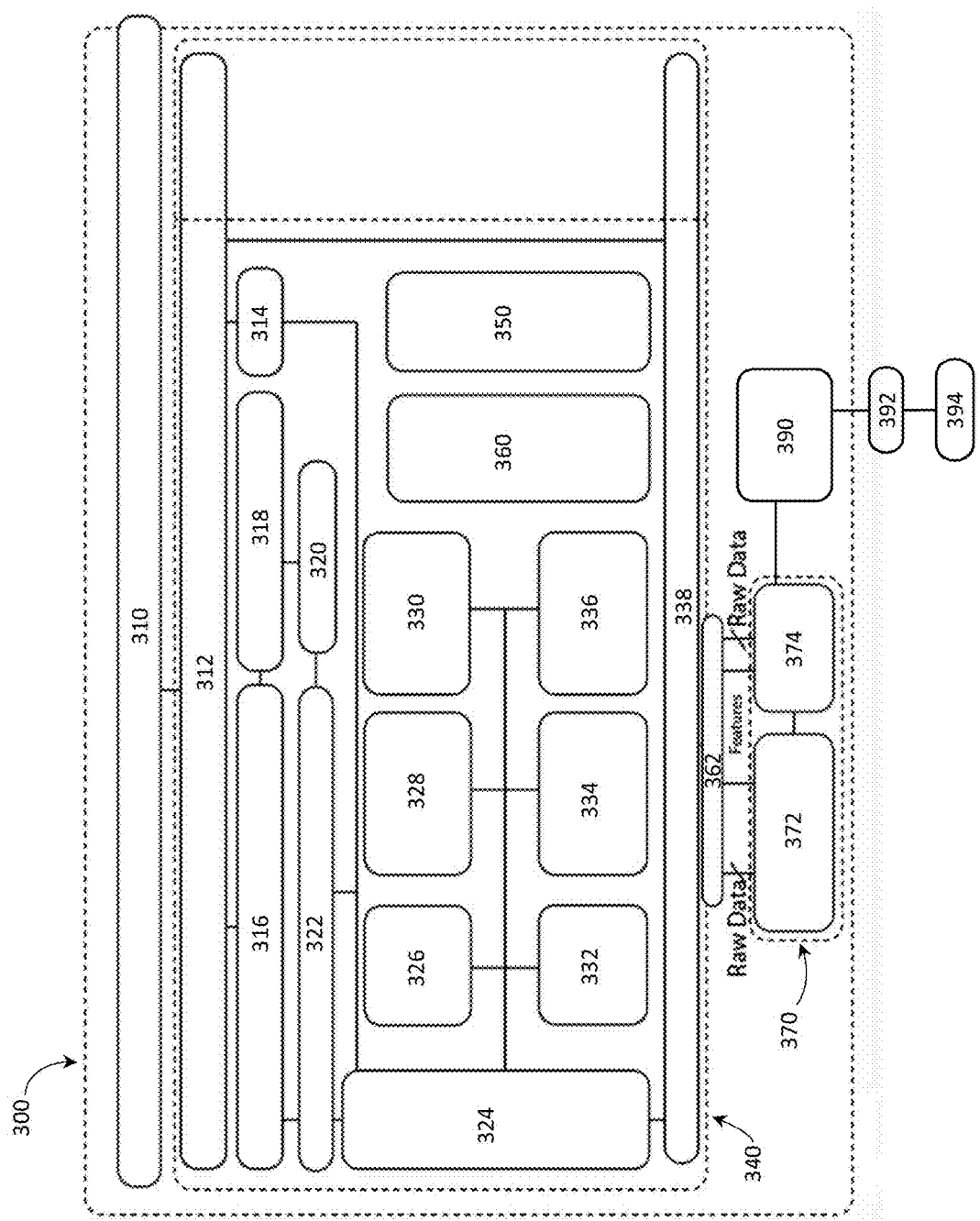
FIG. 3A is a block diagram of an illustrative variation of a second processing system of a biosignal processing system.

FIG. 3A is a block diagram of an illustrative variation of a second processing system of a biosignal processing system. The second processing system (300) may include a second transceiver (310) such as an LVDS receiver configured to communicate with one or more first processing systems (not shown). The second transceiver (310) may be coupled to a digital signal processor (340) comprising a plurality of digital signal processor circuits. The digital signal processor (340) may include a data decoder (312), digital re-referencing circuit (316), a re-referencing buffer (318), averaging circuit (320), accumulation and outlier detection circuit (322), working memory (324), program operations circuit (360), state machine (350), output buffer (338), and digital signal processing circuits. The digital signal processing circuits may include, for example, a first DSP functional circuit (326), a second DSP functional circuit (332), a third DSP functional circuit (334), a first arithmetic functional circuit (328), a second arithmetic functional circuit (330), and a third arithmetic functional circuit (336).

In some variations, the first DSP functional circuit (326) may be a fast Fourier transform circuit (FFT), the first arithmetic functional circuit (328) may be an Arithmetic Logic Unit, the second arithmetic functional circuit (330) may be a thresholding circuit, the second DSP functional circuit (332) may be a digital filtering circuit (FIR), the third DSP functional circuit (334) may be a magnitude and phase extraction circuit, and the third arithmetic functional circuit (336) may be a windowing circuit. The FFT circuit (326) may be configured to determine the frequency content of a signal, the arithmetic circuit (328) may be configured to perform basic mathematical and logic operations on data. In some variations, the arithmetic circuit (328) may comprise a fixed point or floating point circuit. A digital filtering circuit (332) may comprise an M-pole digital FIR filter with adjustable filter parameters. A windowing circuit (336) may be configured to define an operational range over which signals are processed and zeroed out for other data. Additionally, a digital processing circuit may include an averaging circuit configured to calculate a running average of the data.

In some variations, each circuit block may comprise an individual data controller and an individual clock controller configured to be independently controlled to permit satellite and sensor scalability while maintaining low power consumption, thereby enabling higher speed execution through the DSP circuit. This may also permit the biosignal processing system to process biosignal data for a plurality of treatment modes simultaneously (e.g., provide different sets of biosignal characteristics for multi-indication treatment). In some variations, an operating frequency (e.g., clock rate) of the powered ON components may be based on a volume of biosignal data to be processed (e.g., higher operating frequency for large data volumes). In some variations, several identical DSP circuit blocks may execute in parallel at decreased clock rates. The data controllers of each DSP circuit may be configured to ensure that the entire data frame of information is completed within one processing cycle.

The output buffer (338) may be coupled to an input/output interface (362). Data output from the digital signal processor (340) may be input to a third processing system (370). The third processing system (370) may include one or more controllers configured to control a stimulator (390) using the processed digital data output by the second processing system. The controllers may include one or more of an FPGA (372) and microcontroller (374). The stimulator (390) may include one or more leads (392), the leads having one or more stimulating electrodes (394). The second processing system (300) may include additional circuitry configured to execute in parallel with the digital signal processor (340).

In some variations, data frames may be received from the first processing system using the transceiver (310). Each data frame may include sampled data from a set of sensors (e.g., biosignal sensors), as well as a set of biosignal characteristics (e.g., preprocessed analog features) from the analog signal processor. The decoder (312) may be configured to receive the data frame and separate the analog a set of biosignal characteristics from the raw biosignal data. Raw biosignal data is provided to the re-referencing circuit (316). The re-referencing buffer (318) may be mathematically combined with the data frame to generate a viable dataset for downstream processing. Re-referencing improves the common mode rejection beyond what is feasible within the analog front end of the first processing system and may help isolate biosignal activity of interest. Different techniques may be utilized to reduce common mode such as subtracting a known local reference electrode's value or subtracting a running average from all biosignal sensor data. The re-referencing buffer (318) may be filled with arbitrary values (e.g., all zeros such that no additional re-referencing occurs), a running average of each biosignal sensor, or some other arbitrary value (e.g., a biosignal sensor's present value which may be loaded at the same time as the arrival of the data frame).

After re-referencing and averaging, data is provided to outlier detection circuit (322). Outlier detection circuit (322) may be configured to eliminate obviously erroneous data samples that do not make sense within the context of adjacent data samples. These erroneous samples may skew results when they represent irrelevant physiological events. In some variations, an analog set of biosignal characteristics from the analog signal processor may be used to determine whether a data sample is valid (e.g., using analog threshold detection where data greater than a threshold value is likely erroneous). In some variations, invalid data is either removed from the data frame or replaced with average and/or interpolated data. Upon completion of outlier detection, the data is stored until enough samples are received to continue signal processing.

Data may be processed within the digital signal processor (340) in a serial manner in which data retrieved from working memory (324) may be processed by a single circuit block. All unused circuit blocks are powered OFF to save energy. In some variations, for each processing cycle, the digital signal processor (340) may perform one DSP operation from the available circuit blocks. A total of P individual processing steps may be performed, implying that there are P processing cycles over the time course of the arrival of the next data frame. The second processing system may have a clock (e.g., DSPCLK) that has a rate that is equivalent to 1/P. After each processing cycle, the output data may be stored in working memory (324). Upon completion of P processing cycles, a digital set of biosignal characteristics may be stored in the output buffer (338). P may be selected to complete workload processing over a time frame in which the subsequent data frame is aggregated. That is, P may be varied based on a workload size. In some variations, P may generally be less than 32. Accordingly, the output data from any one digital signal processing circuit may be subsequently fed back as an input to another digital signal processing circuit. Therefore, the second processing system (300) may combine these functions as desired. During the processing using one DSP circuit, the remaining DSP circuits are powered OFF and clock gated, thereby enabling low power operation. In some variations, only a subset of the available digital signal processing circuits may be powered ON at all. As such, the second processing system (300) may completely disable unused processing circuits.

In some variations, the output data buffer (338) may be used as input to the third processing system (370) including a controller (e.g., custom decision engine, microcontroller, and/or FPGA) such as a trained classifier configured to selects an appropriate therapeutic pathway using the digital set of biosignal characteristics. This may include one or more of determination to stimulate a region of tissue using the stimulator (390), selection of stimulation waveform shape and stimulation waveform properties. In some variations, the stimulator (390) may comprise a separate device from the biosignal processing system, although FIG. 1 illustrates the biosignal processing system including the stimulator. For example, in treating Parkinson's disease, biosignal characteristics including the phase and amplitude of the beta band (about 12.5 Hz to about 30 Hz) and gamma band (about 30 Hz to about 100 Hz, e.g., about 30 Hz to about 80 Hz, about 40 Hz) of biosignal data may be used to set stimulation patterns and/or parameters of the stimulator (390) to reduce tremors. More specifically, in the Parkinson's disease treatment mode, the digital signal processor may power ON and process data received from the first processing system using the FIR circuit (332), the windowing circuit (336), the FFT circuit (326), and then matrix mathematics for the magnitude and phase circuit (334) to determine a set of biosignal characteristics. The FIR circuit may further be set to a frequency range of about 12.5 Hz to about 30 Hz for the Parkinson's disease treatment mode. The set of biosignal characteristics may be provided as input to the third processing system (370) (e.g., classifier).

Figure 3B:
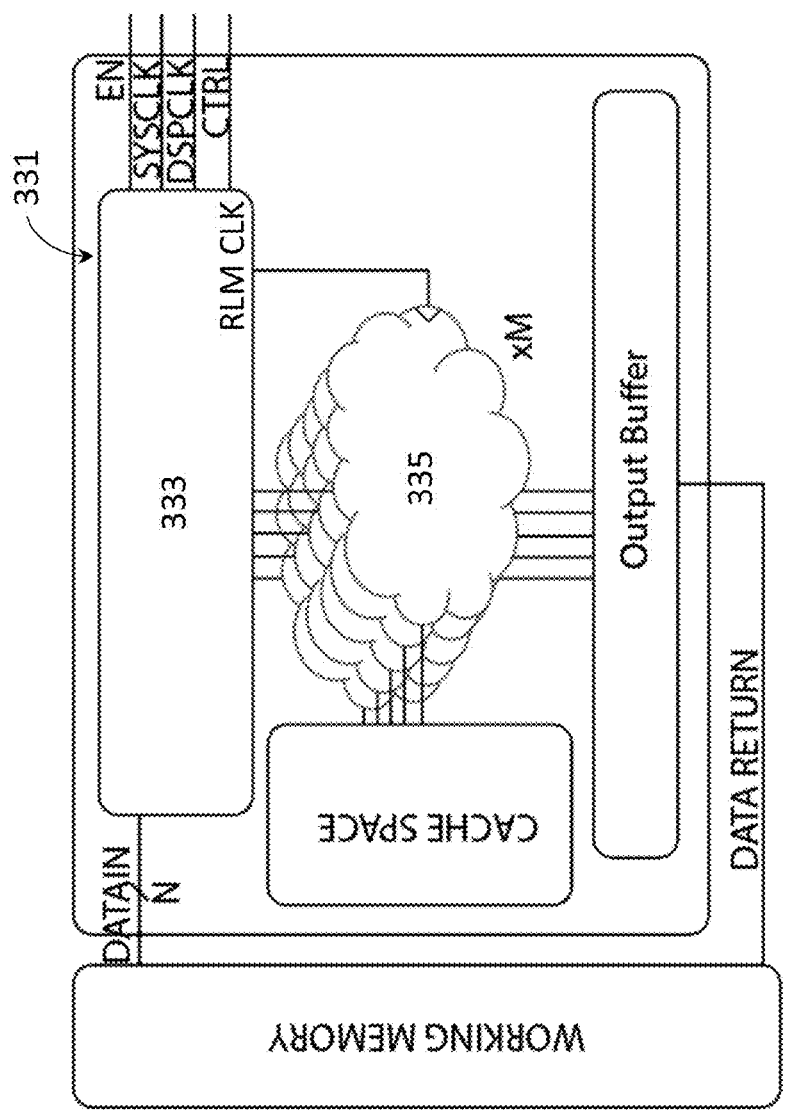
FIG. 3B is a block diagram of an illustrative variation of a digital signal processing circuit of a second processing system.

In some variations, the second processing system (300) may include individual data controllers and clock controllers (an example of which is depicted in FIG. 3B) for each circuit component (e.g., block) such that each component may be powered ON and OFF per application (e.g., treatment mode). In some variations, an operating frequency of the powered ON components may be based on a volume of data to be processed (e.g., higher operating frequency for larger data volumes). FIG. 3B depicts a block diagram of one variation of a data and clock management circuit (331) that may be included with each digital signal processing circuit (e.g., circuits 326-336). The analysis circuit (140) may activate a data and clock management circuit (331) of a signal processing circuit or block through the enable signal EN, which may activate (e.g., turn on) the signal processing circuit or block, and/or set clocking parameters and control. Execution settings may be provided through control bits CTRL, which may specify the functional operation of the processing circuit or block. For example, the CTRL signal may specify that an arithmetic block perform an addition or a summation function, or that an arithmetic block perform a logical AND function, or that a DSP functional block perform an FFT with one frequency bin of information, etc. Data from a working memory (which may be shared across multiple or all signal processing blocks) may be transmitted to a data and clock controller (333). The data and clock controller (333) may specify the logic (e.g., random logic macro or RLM) implementation (335) of the processing circuit or block by powering or activating certain logic macros or subcircuits (and not others). The data and clock controller (333) may also activate the logic implementation (335) in a parallel processing configuration (e.g., multiple, and possibly duplicative, logic macros or subcircuits to process multiple streams of data concurrently) or a serial processing configuration (e.g., a single logic macro or subcircuit to process a single stream of data, executing logic steps sequentially in time), and may adjust a clock rate for the signal processing circuit or block depending on the particular logic implementation. For a given frame or set of biosignal data, the data and clock controller (333) may be configured to calculate the power consumption profile for analyzing the data using a parallel processing configuration (e.g., at a slower clock rate) or a serial processing configuration (e.g., at a higher clock rate), and then select the logic configuration and clock rate such that that power consumption is reduced or optimized while meeting timing constraints or requirements. In some variations, the power consumption profile of a frame or set of biosignal data processed using a particular circuit topology or configuration may be precalculated and/or otherwise predetermined based on an expected data waveform or volume. For example, power consumption profiles or levels for processing a frame of biosignal data using a parallel processing configuration and a serial processing configuration may be calculated before the data is acquired, and may be stored in a memory of the digital signal processing circuit. Then, depending on the volume of data being processed and the amount of parallelism implemented in the processing circuit or block (which may be specified during design or manufacture), the data and clock controller (333) may activate one instance of the logic (e.g., random logic macro or RLM) implementation (335) for serial processing (e.g., a single channel or sequence of logic macros or subcircuits executed sequentially) or more instances of the logic implementation (335) for parallel processing (e.g., multiple channels or sequences of logic macros or subcircuits executing concurrently). The second processing circuit clock DSPCLK may control the construct of the processing cycle, but the data and clock controller (333) may divide the relatively faster system clock SYSCLK to generate a second clock signal (RLMCLK) such that the processing cycle can handle the entire volume of data in the total time allotted to the processing frame. If the volume of biosignal data meets or exceeds a threshold, the data and clock controller (333) may activate several instances of a logic implementation (335) to operate in parallel at a lower clock rate (e.g., where the RLMCLK rate is divided and/or scaled down from the SYSCLK). Alternatively, if the volume of biosignal data is below a threshold, the data and clock controller (333) may activate a single instance of a logic implementation (335) at the higher clock rate (e.g., where the RLMCLK rate is the same as the SYSCLK rate). As described previously, the data and clock controller may calculate a power consumption profile of different possible logic implementations with different clock rates and select the logic implementation that is power-efficient while meeting timing requirements. In some variations, the data and clock controller may calculate the power consumption each instance of a logic macro or subcircuit implemented in parallel and operating at a lower clock rate, and/or calculate the power consumption of a single instance of a logic macro or subcircuit operating at a faster clock rate, and adjust the number of parallel instantiations and/or clock rate to process/analyze an anticipated data load or volume within the specified timing constraints in a power-efficient arrangement.

In some variations, the biosignal processing system may be configured as a fully integrated single system-on-a-chip (SOC). The biosignal processing systems described herein may comprise one or more processors and one or more machine-readable memories in communication with the one or more processors. The processor may incorporate data received from memory and sensor data to control the system. The memory may further store instructions to cause the processor to execute modules, processes and/or functions associated with the system. The controller may be implemented consistent with numerous general purpose or special purpose computing systems or configurations.

The processors described herein may be any suitable processing device configured to run and/or execute a set of instructions or code. The processor may be, for example, a general purpose processor, Field Programmable Gate Array (FPGA), an Application Specific Integrated Circuit (ASIC), and/or the like. The processor may be configured to run and/or execute application processes and/or other modules, processes and/or functions associated with the system. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some variations, the memory may be, for example, a random access memory (RAM), a memory buffer, a hard drive, an erasable programmable read-only memory (EPROM), an electrically erasable read-only memory (EEPROM), a read-only memory (ROM), Flash memory, and the like. The memory may store instructions to cause the processor to execute modules, processes and/or functions associated with the processing system, such as analog signal processing, digital signal processing, and/or stimulation control.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools including custom designed instruction set architectures. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

II. Methods

Also described here are methods for processing biosignal data corresponding to the systems and devices described herein. Generally, the methods described here include serially performing analog and digital preprocessing on a set of biosignal data based on a selected treatment mode. The treatment modes correspond to a set of powered circuit components for processing the raw biosignal data and generating clinically relevant data. The resulting output data may be provided as input to a treatment device to provide, for example, stimulation therapy to treat a condition such as Parkinson's disease.

Figure 4A:
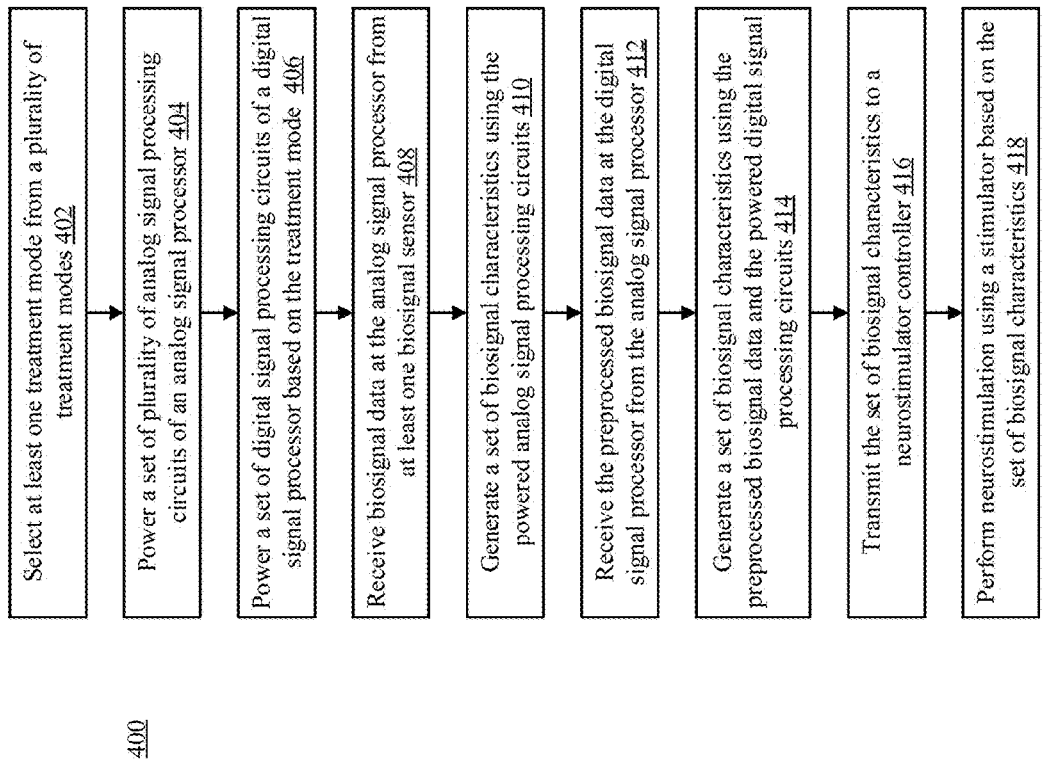
FIGS. 4A-4B are illustrative flowcharts of a variation of a method of processing a biosignal.
Figure 4B:
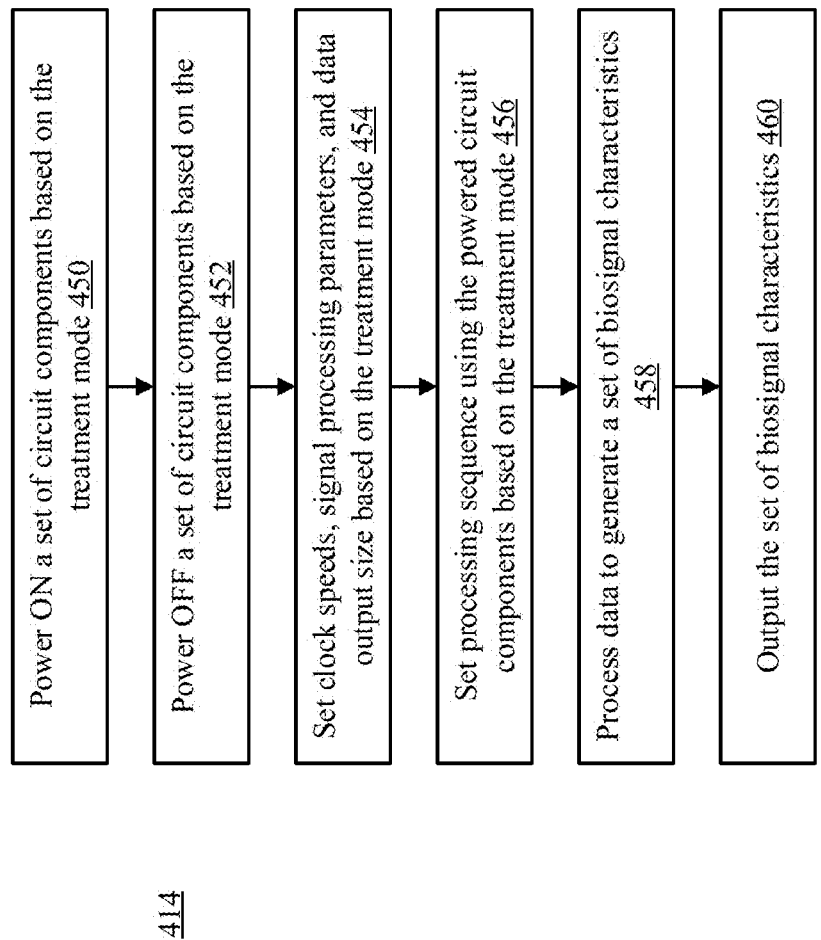

FIGS. 4A-4B are flowcharts that generally describes a method (400) of using a biosignal processing system. The systems, devices, and methods described herein may be used throughout the body to process biosignals and permit therapeutic treatment and/or diagnosis to be performed. The process (400) may begin by selecting at least one treatment mode from a plurality of treatment modes (402). A set of analog signal processing circuits of an analog signal processor may be powered based on the treatment mode (404) and a set of digital signal processing circuits of a digital signal processor may be powered based on the treatment mode (406). Biosignal data may be received at the analog signal processor from at least one biosignal sensor (408). The biosignal data may be preprocessed using the powered analog signal processing circuits (410). The preprocessed biosignal data may be received at the digital signal processor from the analog signal processor (412). A set of biosignal characteristics may be generated using the preprocessed biosignal data and the powered digital signal processing circuits (414). The set of biosignal characteristics may be transmitted to a neurostimulator controller (416). The treatment modes may be configured to power different sets of analog signal processing circuits and digital signal processing circuits. Neurostimulation may be performed based on the neurostimulator control signal generated using the set of biosignal characteristics (418).

In some variations, a digital signal processing pathway comprising a plurality of digital signal processing circuits may be selected based on a selected treatment or processing (or operating) mode. As previously described, the particular digital signal processing circuits that are activated and their connectivity and/or biosignal flow through the digital signal processing circuits may be determined at least in part based on the selected mode and may optionally be determined based on any features or characteristics extracted from the biosignals. At the first digital signal processing circuit of the plurality of digital signal processing circuits, the appropriate biosignal data are read into the data and clock controller, and the appropriate number of parallel functional units (e.g., logic implementations) are activated to handle the volume of data to be processed within the processing frame at a rate determined by the clocking controller. After processing and/or analysis, the data may be stored in an output buffer. Temporary calculations may be stored in a cache (which may be local to each digital signal processing circuit or shared across one or more digital signal processing circuits). After the biosignal data is processed, the output buffer may be flushed out to working memory of the second processing system. Alternatively, the digital signal processing circuit may write back directly to working memory without being stored in a temporary buffer if data volumes are high.

FIG. 4B describes in more detail step (414) of generating a set of biosignal characteristics using the preprocessed biosignal data and the powered digital signal processing circuits. A set of circuit components may be powered ON based on the selected treatment mode (450). A set of circuit components may be powered OFF based on the selected treatment mode (452). Processing circuit clock speeds, signal processing parameters (e.g., frequency range), circuit processing sequence, and data output size (e.g., time frame) may be set based on the treatment mode (454). The data may be processed to generate a set of biosignal characteristics (458). The set of biosignal characteristics may be transmitted to one or more of memory and a third processing system (460).

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to best explain the principles of the invention and its practical applications, and they thereby enable others skilled in the art to best utilize the invention and various implementations with various modifications as are suited to the particular use contemplated. It is intended that the following claims and their equivalents define the scope of the invention.

The invention claimed is:

1. An implantable biosignal processing system comprising:
a first processing system comprising an analog signal processor having a plurality of analog signal processing circuits, wherein the first processing system is configured to connect to a lead comprising one or more biosignal sensors for acquiring and processing electrophysiological data of a brain region of a subject; and
a second processing system in communication with the first processing system, the second processing system comprising a digital signal processor having a power management circuit and a plurality of digital signal processing circuits in communication with the power management circuit, wherein the power management circuit selectively activates and/or deactivates digital signal processing circuits according to a treatment mode of the second processing system to generate a set of electrophysiological data characteristics, and
wherein each digital signal processing circuit has a data and clock controller configured to adjust a clock signal of the digital signal processing circuit based on at least one characteristic of the set of electrophysiological data characteristics.

2. The system of claim 1, wherein activating a digital signal processing circuit of the plurality of digital signal processing circuits comprises powering on the digital signal processing circuit; and deactivating the digital signal processing circuit comprises powering off the digital signal processing circuit.

3. The system of claim 1, wherein the first processing system further comprises a signal processing controller that selectively activates and/or deactivates the plurality of analog signal processing circuits according to the treatment mode.

4. The system of claim 1, wherein the data and clock controller is configured to activate the digital signal processing circuit in a parallel processing configuration if a data volume of the electrophysiological data meets or exceeds a predetermined data volume threshold and to activate the digital signal processing circuit in a serial processing configuration if the data volume is below the predetermined data volume threshold.

5. The system of claim 4, wherein the second processing system has a first clock signal having a first clock rate and each of the plurality of digital signal processing circuits has a second clock signal having a second clock rate generated by the data and clock controller, and wherein when the digital signal processing circuit is in a parallel processing configuration, the second clock rate is less than the first clock rate, and wherein when the digital signal processing circuit is in a serial processing configuration, the second clock rate is the same as the first clock rate.

6. The system of claim 1, wherein the set of electrophysiological data characteristics comprises a characteristic selected from the group consisting of: phase, amplitude, or frequency.

7. The system of claim 1, wherein the set of electrophysiological data characteristics comprises a phase or amplitude of electrophysiological data in a beta band (12.5 Hz 30 Hz) frequency range.

8. The system of claim 1, wherein the set of electrophysiological data characteristics comprises a phase or amplitude of electrophysiological data in a gamma band (30 Hz 100 Hz) frequency range.

9. The system of claim 1, wherein the set of electrophysiological data characteristics comprises action potential count and/or timing and/or amplitude.

10. The system of claim 1, wherein the treatment mode is selected from a group consisting of: neurological disease treatment mode, neurological function augmentation mode, or neural circuitry analysis mode.

11. The system of claim 1, wherein the treatment mode is a Parkinson's Disease treatment mode.

12. The system of claim 1, wherein the treatment mode is an epileptic seizure prevention mode.

13. The system of claim 1, further comprising a neurostimulator in communication with the second processing system and configured to stimulate the brain region of the subject, wherein the second processing system is configured to generate a neurostimulator control signal based on the set of electrophysiological characteristics.

14. The system of claim 13, wherein the lead is a first lead and the system further comprises a second lead comprising one or more biosignal sensors, and a third processing system that is in communication with the second processing system, wherein the third processing system has a second plurality of analog signal processing circuits and is configured to connect to the second lead for acquiring and processing electrophysiological data of a brain region.

15. The system of claim 14, wherein the second processing system is configured to aggregate and process electrophysiological data from the first processing system and the third processing system according to the treatment mode.

16. The system of claim 15, wherein the second processing system is configured to aggregate and process electrophysiological data from the first processing system and the third processing system simultaneously.

17. The system of claim 14, wherein the treatment mode is a first treatment mode and the neurostimulator control signal is a first neurostimulator control signal, and the second processing system is configured to process electrophysiological data from the first processing system according to the first treatment mode to generate the first neurostimulator control signal, and is further configured to process electrophysiological data from the third processing system according to a second treatment mode to generate a second neurostimulator control signal.

18. An implantable biosignal processing system, comprising:
a lead comprising at least one biosignal sensor configured to be coupled to a subject to sense and transmit biosignal data representing electrophysiological activity of the subject;
a first processing system in communication with the lead and configured to acquire the biosignal data from the lead, the first processing system comprising an analog signal processor that has a plurality of analog signal processing circuits configured to be selectively powered to perform different sets of analog processing functions according to a treatment mode; and
a second processing system in communication with the first processing system, the second processing system comprising a digital signal processor and a power management circuit in communication with the digital signal processor, wherein:
the digital signal processor comprises a plurality of digital signal processing circuits configured to be selectively powered by the power management circuit in accordance with the treatment mode to perform different sets of digital processing functions, and each digital signal processing circuit has an independent data and clock controller configured to adjust a clock rate of the digital signal processing circuit based on a biosignal data volume and the treatment mode, and
wherein the powered analog and digital signal processing circuits are configured to serially process the biosignal data to generate a set of biosignal characteristics; and
a neurostimulator in communication with the second processing system and configured to stimulate a predetermined region of tissue using the set of biosignal characteristics.

19. The system of claim 18, wherein the second processing system has a clock generator that generates a system clock signal having a system clock rate, and wherein the clock rate of an individual digital signal processing circuit is different from the system clock rate.

20. The system of claim 18, further comprising a third processing system in communication with the first processing system, the second processing system, and the neurostimulator, wherein the first processing system is configured to transmit the set of biosignal characteristics to the third processing system, and the third processing system is configured to activate the neurostimulator based on the set of biosignal characteristics.

21. The system of claim 18, wherein the biosignal characteristics comprise one or more waveform parameters.

22. The system of claim 18, wherein the first processing system is configured to serially sample a plurality of biosignal sensors of the lead.

23. The system of claim 18, wherein the second processing system is configured to validate the biosignal data from the first processing system using one or more filters.

24. The system of claim 18, wherein the lead is a first lead and the at least one biosignal sensor is a first set of biosignal sensors and the first processing system is a first instance of the first processing system, and wherein the system further comprises a second lead comprising a second set of biosignal sensors and a second instance of the first processing system in communication with the second lead, and wherein the second processing system is communication with the second instance of the first processing system.

25. The system of claim 24, wherein each of first and second instances of the first processing system is configured to process biosignal data acquired from the first and second leads respectively based on different treatment modes, and the second processing system is configured to receive the processed biosignal data and/or biosignal characteristics from the first and second instances of the first processing system simultaneously.

26. The system of claim 24, wherein the second processing system is configured to receive, aggregate, and process the biosignal data from the first and second instances of the first processing system.

27. A method of processing biosignal data, comprising:
selecting at least one treatment mode from a plurality of treatment modes, wherein each treatment mode corresponds to a different set of signal processing parameters and circuit processing sequences;
powering a set of analog signal processing circuits of a first processing system to perform different analog processing functions based on the treatment mode and powering a set of digital signal processing circuits of a second processing system to perform different digital processing functions and processing sequences according to the selected treatment mode;
acquiring biosignal data from a lead comprising at least one biosignal sensor;
transmitting the acquired biosignal data to the first processing system;
processing the biosignal data using the powered analog signal processing circuits;
transmitting the processed biosignal data to the second processing system;
adjusting clock rates for each of the powered digital signal processing circuits according to the selected treatment mode;
generating a set of biosignal characteristics based on the processed biosignal data using the powered digital signal processing circuits; and
transmitting the set of biosignal characteristics to a neurostimulator for use by the neurostimulator in determining waveform parameters for stimulating one or more regions of tissue.

28. The method of claim 27, wherein the treatment modes are configured to power different sets of analog signal processing circuits and digital signal processing circuits.

29. The method of claim 27, further comprising generating a neurostimulator control signal based on the set of biosignal characteristics, and activating the neurostimulator according to the neurostimulator control signal.

30. The method of claim 27, wherein signal processing parameters, circuit processing sequences, and data output size of the digital signal processing circuits are determined based the selected treatment mode.

* * * * *